(12) United States Patent
Yang et al.

(10) Patent No.: US 9,701,603 B2
(45) Date of Patent: Jul. 11, 2017

(54) STREPSESQUITRIOL, PREPARATION METHOD THEREOF, AND APPLICATION THEREOF

(71) Applicant: SOUTH CHINA SEA INSTITUTE OF OCEANOLOGY, CHINESE ACADEMY OF SCIENCES, Guangzhou, Guangdong (CN)

(72) Inventors: Xianwen Yang, Guangzhou (CN); Kun Peng, Guangzhou (CN); Sumei Li, Guangzhou (CN); Gaiyun Zhang, Guangzhou (CN); Jie Li, Guangzhou (CN); Xiuping Lin, Guangzhou (CN); Yonghong Liu, Guangzhou (CN)

(73) Assignee: SOUTH CHINA SEA INSTITUTE OF OCEANOLOGY, CHINESE ACADEMY OF SCIENCES, Guangzhou (CN)

( * ) Notice: Subject to any disclaimer, the term of this patent is extended or adjusted under 35 U.S.C. 154(b) by 0 days.

(21) Appl. No.: 15/034,789

(22) PCT Filed: Dec. 30, 2013

(86) PCT No.: PCT/CN2013/090827
§ 371 (c)(1),
(2) Date: May 5, 2016

(87) PCT Pub. No.: WO2015/066960
PCT Pub. Date: May 14, 2015

(65) Prior Publication Data
US 2016/0368846 A1 Dec. 22, 2016

(30) Foreign Application Priority Data
Nov. 6, 2013 (CN) .......................... 2013 1 0545938

(51) Int. Cl.
*C07C 35/37* (2006.01)
*C12P 7/02* (2006.01)
*C12R 1/465* (2006.01)
*C12P 5/00* (2006.01)
*C12P 15/00* (2006.01)

(52) U.S. Cl.
CPC ............. *C07C 35/37* (2013.01); *C12P 5/007* (2013.01); *C12P 7/02* (2013.01); *C12P 15/00* (2013.01); *C12R 1/465* (2013.01); *C07C 2103/97* (2013.01)

(58) Field of Classification Search
None
See application file for complete search history.

(56) References Cited

U.S. PATENT DOCUMENTS 8,481,592 B2   7/2013   Park et al.
2012/0129924 A1   5/2012   Park et al.

FOREIGN PATENT DOCUMENTS

CN   102143741 A   8/2011
CN   102757908 A   10/2012

OTHER PUBLICATIONS

Yang et al., Strepsesquitriol, a Rearranged Zizaane-Type Sesquiterpenoid from the Deep-Sea-Derived Actinomycete *Streptomyces* sp. SCSIO 10355, Journal of Natural Product, No. 76, pp. 2360-2363, Dec. 11, 2013, w/English abstract (5 pages).

Yang et al., "Sesquiterpenes and an intermediate 1?, 6?, 11-eudesmanetriol in the biosynthesis of geosmin from *Streptomyces* sp.", Acta Phrmaceutica Sinica, No. 47, pp. 364-366, 2012, w/English abstract (5 pages).

International Search Report dated Aug. 12, 2014, issued in counterpart International Application No. PCT/CN2013/090827 (2 pages).

*Primary Examiner* — Michael Barker
(74) *Attorney, Agent, or Firm* — Westerman, Hattori, Daniels & Adrian, LLP

(57) ABSTRACT

The invention discloses a new strepsesquitriol A, a preparation method thereof and an application thereof. Strepsesquitriol A, a structure as shown in Formula (I), is a compound having a new skeleton and strongly inhibiting the formation of LPS-induced TNFα but showing no cytotoxic activity, so it can be used for the preparation of anti-inflammatory drug or act as a precursor of anti-inflammatory drugs, for the treatment of multiple inflammations. Therefore, the invention provides a new candidate compound for the development of anti-inflammatory drugs, and is of great significance for developing Chinese marine drug resources.

Formula (I)

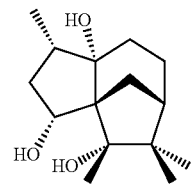

3 Claims, 1 Drawing Sheet

STREPSESQUITRIOL, PREPARATION METHOD THEREOF, AND APPLICATION THEREOF

FIELD OF THE INVENTION

The present invention belongs to the field of natural products, particularly relates to a novel compound, strepsesquitriol, a preparation method thereof and an application thereof.

BACKGROUND OF THE INVENTION

Natural products have always been an important source for the research and development of drugs. Currently, bioactive secondary metabolites with novel carbon skeletons from marine microorganisms, especially those from marine actinomycetes, have gradually become an important direction in the research of natural products.

SUMMARY OF THE INVENTION

The first objective of the present invention is to provide a sesquiterpenoid, a new skeleton compound with anti-inflammatory activity, strepsesquitriol or pharmaceutically acceptable salts thereof.

The strepsesquitriol or pharmaceutically acceptable salts thereof of the present invention have a structure as shown in Formula (I):

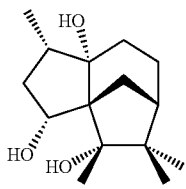

Formula (I)

The second objective of the present invention is to provide a method for preparing the above-mentioned strepsesquitriol, wherein said strepsesquitriol is separated from a fermentation culture of *Streptomyces* sp. SCSIO 10355.

Preferably, the strepsesquitriol is specifically prepared by the following steps:

(a) preparing a fermentation culture of *Streptomyces* sp. SCSIO 10355;

(b) separating a fermentation liquid fraction of the fermentation culture from a mycelia-containing fraction thereof; extracting the fermentation liquid with ethyl acetate, thereby forming a first ethyl acetate extract; performing concentration of the first ethyl acetate extract to obtain an extract A; leaching the mycelia with ethanol, and recovering the ethanol from the mycelia leaching solution wherein an aqueous solution remains after said recovering of ethanol; extracting the aqueous solution with ethyl acetate, thereby forming a second ethyl acetate extract; performing concentration of the second ethyl acetate extract to obtain an extract B; mixing the extract A and the extract B to obtain a crude extract;

(c) subjecting the crude extract to medium-pressure liquid chromatography over octadecylsilyl silica gel (ODS) and performing a gradient elution with water:methanol as an eluent in a volume ratio that begins at 100:0 and ends at 0:100; collecting a first fraction from said gradient elution when the water:methanol ratio is 1:1; purifying the first fraction by performing column chromatography over sephadex (sephadex LH-20) on the first fraction, eluting with chloroform:methanol in a volume ratio of 1:1 to obtain a second fraction; performing preparative thin-layer chromatography on the second fraction with chloroform:acetone in a volume ratio of 10:1 as a developing solvent to obtain a third fraction, and purifying the third fraction to obtain the strepsesquitriol.

The fermentation culture of *Streptomyces* sp. SCSIO 10355 prepared in step (a) is preferably prepared by the following steps: inoculating an activated *Streptomyces* sp. SCSIO 10355 into a seed culture medium, culturing the inoculated seed culture medium at 28° C. and 200 rpm for 72 h to obtain a seed liquid; inoculating the seed liquid into a fermentation culture medium according to a 10% (V/V) inoculation amount, performing shaking culture of the inoculated fermentation culture medium at 28° C. and 180 rpm for 10 days to prepare the fermentation culture, wherein both formulae of the seed culture medium and the fermentation culture medium are as follows: each liter of the culture medium contains 15 g of soluble starch, 5 g of soybean meal, 15 g of peptone, 15 g of glycerin, 2 g of $CaCO_3$, 30 g of marine salt and the balance of water, and the pH is 7.4.

The third objective of the present invention is to provide an application of *Streptomyces* sp. SCSIO 10355 in the preparation of the above-mentioned strepsesquitriol.

The inventors have found in experiments that the compound strepsesquitriol has a strong inhibitory effect on the formation of LPS-induced TNFα (LPS is short for lipopolysaccharide, and TNF is short for Tumor Necrosis Factor) with an inhibition rate of 35.4% at a concentration of 100 μM, but shows no cytotoxic activity to RAW264.7 cells at the same concentration, thus it is expected to be developed into a new non-toxic anti-inflammatory drug.

Therefore, the fourth objective of the present invention is to provide an application of strepsesquitriol in the preparation of anti-inflammatory drug.

The fifth objective of the present invention is to provide an anti-inflammatory drug, comprising an effective amount of strepsesquitriol as an active ingredient and a pharmaceutically acceptable carrier.

In conclusion, *Streptomyces* sp. SCSIO 10355 of the present invention can produce a novel sesquiterpenoid compound with anti-inflammatory activity, strepsesquitriol. Since the compound has a strong inhibitory effect on LPS-induced TNFα, it can be used for the preparation of anti-inflammatory drugs, as an ideal candidate compound for the development of high-effective, low-toxic anti-inflammatory drugs.

During the research of secondary metabolites of marine actinomycetes, we have obtained a novel sesquiterpenoid compound, strepsesquitriol. Said compound has a rare spirocaged structure and a strong anti-inflammatory effect, and shows no cytotoxicity in effective doses. Therefore, it is an ideal candidate compound for the development of anti-inflammatory drugs with novel structures and potent activity. Deep-sea *Streptomyces* sp. SCSIO 10355 of the present invention was collected in China General Microbiological Culture Collection Center (CGMCC, address: Institute of Microbiology, Chinese Academy of Sciences, No. 3, Courtyard 1, Beichen West Road, Chaoyang District, Beijing) with the collection number of CGMCC No. 4.7120 deposited on Sep. 27, 2013.

DETAILED DESCRIPTION OF THE EMBODIMENTS

Figure 1:
FIG. 1 shows key $^1H$—$^1H$ COSY (bold) correlations and HMBC (arrow) correlations of strepsesquitriol A in $CD_3OD$ (left) and (DMSO-$d_6$)

The following embodiments further illustrate the present invention, rather than limiting the present invention.

Embodiment 1: Preparation and Separation of Strepsesquitriol

1. Seed culture medium (as well as fermentation culture medium): each liter of culture medium comprised (by weight) 15 g of soluble starch, 5 g of soybean meal, 15 g of peptone, 15 g of glycerin, 2 g of $CaCO_3$, 30 g of marine salt and the balance of water, and the pH was 7.4. The above components were uniformly mixed, and sterilized for 30 min at 121° C. for later use.

2. Fermentation 2.1 Seed culture: inoculating an activated *Streptomyces* sp. SCSIO 10355 into 250 mL conical culture flasks, each flask containing 50 mL of the seed culture medium, culturing the inoculated seed culture medium at 28° C. and 200 rpm for 72 h to obtain a seed liquid.

2.2. Fermentation culture: inoculating the seed liquid into 20 L of fermentation medium according to an inoculation amount with a volume fraction of 10%, and performing shaking culture of the inoculated fermentation culture medium at 28° C. and 180 rpm for 10 days to prepare a fermentation culture.

3. Extraction: separating a fermentation liquid fraction of the fermentation culture from a mycelia-containing fraction thereof by centrifugation (3500 rpm, 8 min). Extracting the fermentation liquid for four times with ethyl acetate, collecting ethyl acetate extract and performing decompressing distillation concentration to obtain an extract A (21.5 g); leaching the mycelia with ethanol for three times, 15 min each time, collecting mycelia leaching solution, and performing decompressing to recover the ethanol from the mycelia leaching solution wherein an aqueous solution remains after said recovering of ethanol; extracting the aqueous solution with ethyl acetate, performing decompressing distillation concentration of ethyl acetate extract to obtain an extract B (10.4 g). Mixing the extract A and the extract B to obtain a crude extract (31.9 g).

4. Separation and Identification of Strepsesquitriol

Subjecting the crude extract (31.9 g), prepared by mixing extra A and the extra B, to medium-pressure liquid chromatography over octadecylsilyl silica gel (YMC-GEL ODS-A), performing a gradient elution on the ODS column containing said extract by eluting the silica gel column with water:methanol in a volume ratios that begins at 100:0 and ends at 0:100; collecting a 50% methanol (i.e., the volume ratio of methanol:water is 1:1) fraction (0.7 g); performing gel column chromatography (over Sephadex LH-20) on the 50% methanol fraction wherein the gel column chromatography is eluted with chloroform:methanol in a volume ratio of 1:1 to obtain a second fraction; performing preparative thin-layer chromatography (prep. TLC) on the second fraction, wherein development is conducted for three times with chloroform-acetone (volume ratio of 10:1) as a developing solvent, collecting compound having a Rf value (Retention Factor Value) of about 0.5, and thereby strepsesquitriol (5.4 mg) was obtained.

Structural Identification: strepsesquitriol was obtained as a white amorphous powder, and its NMR data was as shown in Table 1; the high resolution mass spectrum HRESIMS thereof presented an adduct ion peak at m/z 277.1776 ([M+Na]), which suggested the molecular formula $C_{15}H_{26}O_3$, accounting for three degrees of unsaturation. The $^1H$ NMR spectrum exhibited one oxygenated methine at $\delta_H$ 3.79 (1H, d, J=6.3 Hz, H-2), and one doublet and three singlet methyls ($\delta_H$ 1.02, 1.03 s, 1.09 s, and 1.48 s, each 3H, Me-4a, 9a, 9b, 10a), wherein these signal peaks were supported by resonances in $^{13}C$ NMR spectrum at $\delta_C$ 80.1 (CH, C-2), 14.6 ($CH_3$, C-4a), 23.3 ($CH_3$, C-10α), 21.8 ($CH_3$, C-9b), and 30.2 ($CH_3$, C-9a). All together, the $^1H$, $^{13}C$ and DEPT NMR spectrum gave 15 signals including four quaternary carbons [two were oxygenated: $\delta_C$ 87.3 (C-5) and 85.0 (C-10)], three methines, four methylenes and four methyls (Table 1). Given that the 15 carbons are all $sp^3$ hybridized carbons, strepsesquitriol was concluded to bear three rings in its structure.

In the $^1H$—$^1H$ COSY spectrum thereof, we found two correlated long chains: H-2 ($\delta_H$ 3.79)/H-3β ($\delta_H$ 2.41)/H-4 ($\delta_H$ 2.21)/H-4a ($\delta_H$ 1.02) and H-6β ($\delta_H$ 1.87)/H-7β ($\delta_H$ 1.43)/H-7α ($\delta_H$ 1.84)/H-8 ($\delta_H$ 1.52)/H-11β ($\delta_H$ 1.13), which allowed the assembly of two segments: C-2/C-3/C-4/C-4a and C-6/C-7/C-8/C-11. These two fragments could be connected based on the key HMBC correlations originated from four methyls, one oxymethine (H-2), and two methylenes (H-6 and H-11), which constructed the planar structure as 4,9,9,10-tetramethyl-2,5,10-trihydroxyltricyclo[6.2.1.0$^{1,5}$] undecane. For further confirmation on the structure, we dissolved strepsesquitriol A in DMSO-$d_6$, performed spectrum analysis a second time and found the correlations of 5-OH ($\delta_H$ 5.61 s) to C-5/C-4/C-1/C-6, 2-OH ($\delta_H$ 4.11, d, J=9.9 Hz) to C-2/C-1, and 10-OH ($\delta_H$ 5.43 s) to C-1/C-10/C-9, which established the planar structure of strepsesquitriol (FIG. 1).

Figure 2:
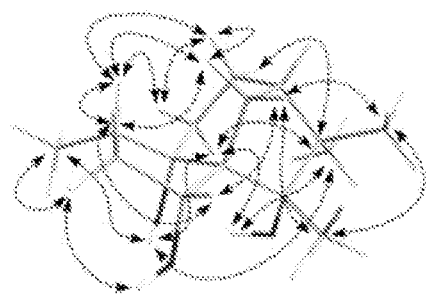
FIG. 2 shows key NOESY correlations of strepsesquitriol.

The assignment of relative configuration of strepsesquitriol was achieved by analysis of NOESY spectrum in the solvent DMSO-$d_6$. As shown in FIG. 2, H-3β was correlated to H-2/H-11β/H-4, H-4 was correlated to H-6β/H-7β/H-11β, and H-11α was correlated to H-2/H-9a/H-10a, while H-3α was correlated to 2-OH/H-4a, H-4a was correlated to 5-OH, 5-OH was correlated to H-6Oα/H-9b, and H-9b was correlated to H-7α/H-6α/10-OH, thereby indicating that H-2/H-3β/H-4/H-6β/H-7β/H-11/H-9a/H-10a were cofacial, just opposite to 2-OH/H-3α/H-4a/5-OH/H-6α/H-7α/H-9b/10-OH. Since H-6α was correlated to H-9b/10-OH, H-11β was correlated to H-7β, and H-11α was correlated to H-9a/H-10a respectively, ring B was deduced to be in a chair configuration, while ring C was in an envelope configuration. In addition, H-11β was correlated to H-4/H-3β, so ring A was deduced to be in an envelope configuration as well. On the basis of the above evidence, strepsesquitriol was determined to be 4α,9,9,10β-tetramethyl-2α,5α,10α-trihydroxyltricyclo[6.2.1.0$^{1,5}$]undecane. Quantum-chemical calculations were performed, and theoretical optical rotation values (theoretical OR) of (1R,2R,4S,5S,8S,10S)- and (1S,2S,4R,5R,8R,10R)-4,9,9,10-tetramethyl-2,5,10-trihydroxyltricyclo[6.2.1.0$^{1,5}$]undecane were respectively +28.5 and −28.6, and since the measured values (+21.0) was close to +28.5 and just opposite to −28.6, the absolute configuration thereof was determined to be (1R,2R,4S,5S,8S,10S)-4,9,9,10-tetramethyl-2,5,10-trihydroxyltricyclo[6.2.1.0$^{1,5}$]undecane.

The structure of strepsesquitriol was proposed to be as shown in Formula (I):

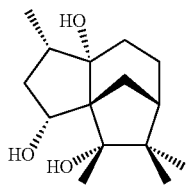

Formula (I)

TABLE 1

$^1$H— and $^{13}$C-NMR data of strepsesquitriol

| no. | 1$^a$ δC | δH | 1$^b$ δC | δH |
|---|---|---|---|---|
| 1 | 63.4 C | | 61.5C | |
| 2 | 80.1 CH | 3.79(d, 6.3) | 77.7CH | 3.65(dd, 9.8, 6.3) |
| 3 | 43.4CH$_2$ | α)1.37(dd, 14.7, 6.3) | 42.3CH$_2$ | α)1.23(dd, 14.4, 6.3) |
| | | β)2.41(ddd, 14.7, 10.9, 6.4) | | β)2.30(ddd, 14.4, 10.8, 6.4) |
| 4 | 38.8CH | 2.21(ddq, 10.9, 6.9, 6.4) | 36.7CH | 2.11(ddq, 10.8, 6.7, 6.4) |
| 4a | 14.6CH$_3$ | 1.02(d, 7.1) | 14.4CH$_3$ | 0.93(d, 6.9) |
| 5 | 87.3C | | 84.9C | |
| 6 | 31.3CH$_2$ | α)1.78(dd, 14.2, 7.8) | 30.1CH$_2$ | α)1.64(dd, 13.9, 7.7) |
| | | β)1.87(dt, 14.2, 7.8) | | β)1.75(dt, 13.9, 7.8) |
| 7 | 27.1CH$_2$ | α)1.84m | 25.7CH$_2$ | α)1.70 m |
| | | β)1.43m | | β)1.34(dddd, 12.8, 8.1, 6.9, 2.8) |
| 8 | 46.2CH | 1.52m | 44.0CH | 1.42m |
| 9 | 47.4C | | 45.9C | |
| 9a | 30.2CH$_3$ | 1.03s | 29.5CH$_3$ | 0.94s |
| 9b | 21.8CH$_3$ | 1.09s | 21.4CH$_3$ | 1.00s |
| 10 | 85.0C | | 83.1C | |
| 10a | 23.3CH$_3$ | 1.48s | 22.6CH$_3$ | 1.39s |
| 11 | 36.5CH$_2$ | α)1.54m | 34.8CH$_2$ | α)1.43(ddd, 12.8, 4.8, 2.3) |
| | | β)1.13(d, 12.0) | | β)1.02(dd, 12.8, 2.9) |
| 2-OH | | | | 4.11(d, 9.9) |
| 5-OH | | | | 5.61s |
| 10-OH | | | | 5.43s |

$^a$is measured by Bruker Avance 500 NMR chromatograph, and the solvent is CD$_3$OD;
$^b$is measured by Bruker Avance 600 NMR chromatograph, and the solvent is DMSO-d$_6$.

Embodiment 2: Determination of Anti-Inflammatory Activity of Strepsesquitriol

As for determination of inhibitory activity of Strepsesquitriol on the formation of lipopolysaccharide (LPS)-induced TNFα in RAW264.7 macrophages, please refer to the references (Fan, S. Y.; Zeng, H. W.; Pei, Y. H.; Li. L.; Ye, J.; Pan, Y. X.; Zhang, J. G.; Yuan, X.; Zhang, W. D. The anti-inflammatory activities of an extract and compounds isolated from *Platycladus orientalis* (Linnaeus) Franco in vitro and ex vivo *J Ethnopharmacol* 2012, 141, 647-652) ENREF 3. The results were as shown in Table 2: at a concentration of 100 μM, strepsesquitriol showed a strong inhibitory activity with an inhibition rate of 35.4%, while the positive control drug N-p-tosyl-1-phenylalanine chloromethyl ketone showed an inhibition rate of 60.6% at a same dose. In addition, at a concentration of 100 μM, strepsesquitriol showed no cytotoxic activity, thereby suggesting that it can be used for the preparation of low-toxicity and highly effective anti-inflammatory drugs.

TABLE 2

Inhibitory activity of strepsesquitriol on the formation of LPS-induced TNFα production

| Group | Concentration (μM) | Inhibition rate (%) |
|---|---|---|
| TPCK$^a$ | 100.0 | 60.6 ± 0.9 |
| Strepsesquitriol A | 3.6 | 3.4 ± 2.8 |
| | 11.0 | 8.0 ± 1.6 |
| | 33.0 | 30.6 ± 1.4 |
| | 100.0 | 35.4 ± 0.6 |

$^a$TPCK: N-p-tosyl-1-phenylalanine chloromethyl ketone, a positive control drug

The invention claimed is:
1. A method for preparing a strepsesquitriol, having a structure as shown in Formula (I):

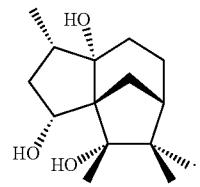

Formula (I)

wherein said strepsesquitriol is separated from a fermentation culture of *Streptomyces* sp. SCSIO 10355.

2. The method of claim 1, wherein the strepsesquitriol is specifically prepared by the following steps:
  (a) preparing a fermentation culture of *Streptomyces* sp. SCSIO 10355;
  (b) separating a fermentation liquid fraction of the fermentation culture from a mycelia-containing fraction thereof, extracting the fermentation liquid with ethyl acetate, thereby forming a first ethyl acetate extract; performing concentration of the first ethyl acetate extract to obtain an extract A; leaching the mycelia from the mycelia-containing fraction of the fermentation liquid with ethanol to form a mycelia leaching solution, and recovering the ethanol from the mycelia leaching solution wherein an aqueous solution remains after said recovering of ethanol; extracting the aqueous solution with ethyl acetate, thereby forming a second ethyl acetate extract; performing concentration of the second ethyl acetate extract to obtain an extract B; mixing the extract A and the extract B to obtain a crude extract;
  (c) subjecting the crude extract to medium-pressure liquid chromatography over octadecylsilyl silica gel and performing a gradient elution with water:methanol as an eluent in a volume ratios that begins at 100:0 and ends at 0:100; collecting a first fraction from said gradient elution when the water:methanol ratio is 1:1; purifying the first fraction by performing column chromatography over sephadex on the first fraction, eluting with chloroform:methanol in a volume ratio of 1:1 to obtain a second fraction; performing preparative thin-layer chromatography on the second fraction with chloroform:acetone in a volume ratio of 10:1 as a developing solvent to obtain a third fraction, and purifying the third fraction to obtain the strepsesquitriol.

3. The method of claim 2, wherein the fermentation culture of *Streptomyces* sp. SCSIO 10355 prepared in step (a) is prepared by the following steps:

inoculating an activated *Streptomyces* sp. SCSIO 10355 into a seed culture medium to form a inoculated seed culture medium, culturing the inoculated seed culture medium at 28° C. and 200 rpm for 72 h to obtain a seed liquid;

inoculating the seed liquid into a fermentation culture medium according to a 10% inoculation amount, performing shaking culture of the inoculated fermentation culture medium at 28° C. and 180 rpm for 10 days to prepare the fermentation culture, wherein both formulae of the seed culture medium and the fermentation culture medium are as follows: each liter of each culture medium contains 15 g of soluble starch, 5 g of soybean meal, 15 g of peptone, 15 g of glycerin, 2 g of $CaCO_3$, 30 g of marine salt, and the balance of water, and the pH is 7.4.

* * * * *